United States Patent
Ichikawa et al.

(10) Patent No.: US 11,702,779 B2
(45) Date of Patent: Jul. 18, 2023

(54) SPUNBONDED NON-WOVEN FABRIC, SANITARY MATERIAL, AND METHOD OF MANUFACTURING SPUNBONDED NON-WOVEN FABRIC

(71) Applicant: MITSUI CHEMICALS, INC., Tokyo (JP)

(72) Inventors: Taiichiro Ichikawa, Tokyo (JP); Akio Matsubara, Ichihara (JP); Koichi Shimada, Chiba (JP); Shigeyuki Motomura, Chiba (JP)

(73) Assignee: MITSUI CHEMICALS, INC., Tokyo (JP)

( * ) Notice: Subject to any disclaimer, the term of this patent is extended or adjusted under 35 U.S.C. 154(b) by 205 days.

(21) Appl. No.: 17/424,577

(22) PCT Filed: Jan. 30, 2020

(86) PCT No.: PCT/JP2020/003483
§ 371 (c)(1),
(2) Date: Jul. 21, 2021

(87) PCT Pub. No.: WO2020/158875
PCT Pub. Date: Aug. 6, 2020

(65) Prior Publication Data
US 2022/0081814 A1   Mar. 17, 2022

(30) Foreign Application Priority Data
Jan. 30, 2019   (JP) .................................. 2019-014680

(51) Int. Cl.
*D04H 1/541*   (2012.01)
*D04H 1/56*   (2006.01)
(Continued)

(52) U.S. Cl.
CPC ......... *D04H 1/5416* (2020.05); *D04H 1/4291* (2013.01); *D04H 1/56* (2013.01); *D04H 3/007* (2013.01); *D04H 3/16* (2013.01)

(58) Field of Classification Search
CPC ...... D04H 1/5416; D04H 1/56; D04H 1/4291; D04H 3/007; D04H 3/16
See application file for complete search history.

(56) References Cited

U.S. PATENT DOCUMENTS

2008/0014819 A1   1/2008 Suzuki et al.
2011/0318986 A1*  12/2011 Pourdeyhimi ......... D04H 1/541
                                                    264/103
(Continued)

FOREIGN PATENT DOCUMENTS

JP   H09512313 A   12/1997
JP   2002-146631 A   5/2002
(Continued)

OTHER PUBLICATIONS

English translation of WO-2018131549-A1 to Narita et al. obtained from PE2E database. (Year: 2018).*

*Primary Examiner* — Jeremy R Pierce
(74) *Attorney, Agent, or Firm* — Buchanan Ingersoll & Rooney PC

(57) ABSTRACT

A spunbonded non-woven fabric includes a fiber including a propylene homopolymer having a melting point of 140° C. or more, a polyethylene having a density of from 0.941 $g/cm^3$ to 0.970 $g/cm^3$, and at least one polymer selected from the group consisting of a polymer represented in (I) and a polymer represented in (II). In the spunbonded non-woven fabric, the fiber includes a sea-island structure, and the percentage of an island phase having a diameter of from 0.12 µm to less than 0.63 µm with respect to an island phase in a cross section orthogonal to the axis direction of the fiber on a number basis is 30% or more. (I) represents a random
(Continued)

copolymer of propylene and at least one selected from ethylene or an α-olefin having a carbon number of from 4 to 20. (II) represents a propylene homopolymer with a melting point of less than 120° C.

11 Claims, 5 Drawing Sheets

(51) Int. Cl.
*D04H 1/4291* (2012.01)
*D04H 3/007* (2012.01)
*D04H 3/16* (2006.01)

(56) References Cited

U.S. PATENT DOCUMENTS

| | | | |
|---|---|---|---|
| 2015/0233031 A1* | 8/2015 | Kunimoto | D04H 3/16 442/365 |
| 2017/0314174 A1* | 11/2017 | Ichikawa | D04H 3/16 |
| 2018/0213852 A1* | 8/2018 | Matsubara | D04H 3/007 |
| 2020/0362492 A1* | 11/2020 | Ichikawa | D04H 3/16 |

FOREIGN PATENT DOCUMENTS

| | | | | |
|---|---|---|---|---|
| JP | 2016-517485 A | 6/2016 | | |
| WO | 9616216 A1 | 5/1996 | | |
| WO | 2006/057369 A1 | 6/2006 | | |
| WO | 2014050965 A1 | 4/2014 | | |
| WO | 2014/159724 A1 | 10/2014 | | |
| WO | 2017006972 A1 | 1/2017 | | |
| WO | WO-2018131549 A1 * | 7/2018 | | A01N 25/02 |

* cited by examiner

SPUNBONDED NON-WOVEN FABRIC, SANITARY MATERIAL, AND METHOD OF MANUFACTURING SPUNBONDED NON-WOVEN FABRIC

TECHNICAL FIELD

The present disclosure relates to a spunbonded non-woven fabric, a sanitary material, and a method of manufacturing a spunbonded non-woven fabric.

BACKGROUND ART

In recent years, non-woven fabrics have been widely used in various applications because the non-woven fabrics have been excellent in permeability and flexibility. Examples of typical applications of the non-woven fabric include absorbent articles such as paper diapers and sanitary napkins, sanitary masks, medical gauze, and base fabrics for fomentation materials.

It is demanded that such a non-woven fabric has, for example, extensibility depending on a place in which the non-woven fabric is used.

For example, Japanese National-Phase Publication (JP-A) No. H9-512313 proposes a technology for a contact-type expandable non-woven fabric with favorable expandability, including a polyethylene and a propylene polymer, as a non-woven fabric included in a composite non-woven fabric.

International Publication No. WO 2014/050965 proposes a spunbonded non-woven fabric including a composition including two or more polypropylenes, of which the melting points are different from each other, and a specific fatty acid amide, as a non-woven fabric having flexibility.

International Publication No. WO 2017/006972 proposes a spunbonded non-woven fabric including a polymer selected from the group consisting of a random copolymer of an α-olefin having a specific carbon number and a propylene, and a propylene homopolymer having a comparatively low-melting-point and specific meso-pentad and racemic pentad fractions, as well as a propylene homopolymer having a comparatively high melting point and a polyethylene, as a spunbonded non-woven fabric having a favorable heat-sealing property at low temperature and favorable stretching processing suitability.

SUMMARY OF INVENTION

Technical Problem

In the contact-type expandable non-woven fabric described in JP-A No. H9-512313, improvement in extensibility may be demanded for using the contact-type expandable non-woven fabric as a single non-woven fabric although an aspect including a second expandable layer is considered as a composite non-woven fabric.

In the spunbonded non-woven fabric described in International Publication No. WO 2014/050965, improvement in extensibility may be demanded.

In the spunbonded non-woven fabric described in International Publication No. WO 2017/006972, more improvement in extensibility may be demanded.

In accordance with an embodiment of the present invention, a spunbonded non-woven fabric excellent in extensibility and a sanitary material using the spunbonded non-woven fabric are provided without using a thermoplastic polyurethane elastomer.

In accordance with another embodiment of the invention, a method of manufacturing a spunbonded non-woven fabric excellent in extensibility is provided.

Solution to Problem

The disclosure includes the following embodiments.

<1>

A spunbonded non-woven fabric, comprising a fiber comprising: a propylene homopolymer having a melting point of 140° C. or more; a polyethylene having a density of from 0.941 g/cm$^3$ to 0.970 g/cm$^3$; and at least one polymer selected from the group consisting of a polymer specified in the following (I) and a polymer specified in the following (II), wherein the fiber comprises a sea-island structure, and a percentage of an island phase having a diameter of from 0.12 µm to less than 0.63 µm with respect to an entire island phase in a cross section orthogonal to an axis direction of the fiber on a number basis is 30% or more:

(I) a random copolymer of propylene and at least one selected from ethylene or an α-olefin having a carbon number of from 4 to 20, and (II) a propylene homopolymer with a melting point of less than 120° C., satisfying the following (a) to (f):

(a) [mmmm]=from 20% by mol to 60% by mol,
(b) [rrrr]/(1−[mmmm])≤0.1,
(c) [rmrm]>2.5% by mol,
(d) [mm]×[rr]/[mr]$^2$≤2.0,
(e) weight-average molecular weight (Mw)=from 10,000 to 200,000, and
(f) molecular weight distribution (Mw/Mn)<4, wherein, in (a) to (d), [mmmm] represents a meso-pentad fraction, [rrrr] represents a racemic pentad fraction, [rmrm] represents a racemic meso-racemic meso-pentad fraction, each of [mm], [rr], and [mr] represents a triad fraction, and Mn represents a number-average molecular weight.

<2>

The spunbonded non-woven fabric according to <1>, wherein a percentage of an island phase having a diameter of 0.63 µm or more on a number basis is 10% or less.

<3>

The spunbonded non-woven fabric according to <1> or <2>, wherein a percentage of an island phase having a diameter of less than 0.12 µm on a number basis is 70% or less.

<4>

The spunbonded non-woven fabric according to any one of <1> to <3>, wherein a content of the polyethylene is from 1.0% by mass to 15.0% by mass with respect to a total amount of the fiber.

<5>

The spunbonded non-woven fabric according to any one of <1> to <4>, wherein a content of at least one polymer selected from the group consisting of the polymer specified in (I) and the polymer specified in (II) is from 5.0% by mass to 30.0% by mass with respect to a total amount of the fiber.

<6>

The spunbonded non-woven fabric according to any one of <1> to <5>, wherein a content of the propylene homopolymer having a melting point of 140° C. or more is from 55.0% by mass to 90.0% by mass with respect to a total amount of the fiber.

<7>

The spunbonded non-woven fabric according to any one of <1> to <6>, wherein the fiber includes a fatty acid amide having a carbon number of from 15 to 22, and a content of the fatty acid amide having a carbon number of from 15 to 22 is from 0.1% by mass to 5.0% by mass with respect to a total amount of the fiber.

<8>

The spunbonded non-woven fabric according to any one of <1> to <7>, wherein the polymer specified in (I) is a random copolymer comprising at least a constitutional unit derived from propylene and a constitutional unit derived from ethylene.

<9>

A sanitary material including the spunbonded non-woven fabric according to any one of <1> to <8>.

<10>

A method of manufacturing a spunbonded non-woven fabric, the method comprising extruding a composition comprising: a propylene homopolymer having a melting point of 140° C. or more; a polyethylene having a density of from 0.941 g/cm³ to 0.970 g/cm³; and at least one polymer selected from a group consisting of a polymer specified in the following (I) and a polymer specified in the following (II) such that an amount of the composition extruded from an extruding machine A and an extruding machine B is 85:15 to 55:45 (extruding machine A: extruding machine B) on a mass basis:

(I) a random copolymer of propylene and at least one selected from ethylene or an α-olefin having a carbon number of from 4 to 20, and (II) a propylene homopolymer with a melting point of less than 120° C., satisfying the following (a) to (f), (a) [mmmm]=from 20% by mol to 60% by mol,
(b) [rrrr]/(1−[mmmm])≤0.1,
(c) [rmrm]>2.5% by mol,
(d) [mm]×[rr]/[mr]²≤2.0,
(e) weight-average molecular weight (Mw)=from 10,000 to 200,000, and
(f) molecular weight distribution (Mw/Mn)≤4, wherein in (a) to (d), [mmmm] represents a meso-pentad fraction, [rrrr] represents a racemic pentad fraction, [rmrm] represents a racemic meso-racemic meso-pentad fraction, each of [mm], [rr], and [mr] represents a triad fraction, and Mn represents a number-average molecular weight.

<11>

The method of manufacturing a spunbonded non-woven fabric according to <10>, wherein a bore A of the extruding machine A is larger than a bore B of the extruding machine B.

Advantageous Effects of Invention

In accordance with an embodiment of the invention, a spunbonded non-woven fabric excellent in extensibility and a sanitary material using the spunbonded non-woven fabric are provided.

In accordance with another embodiment of the invention, a method of manufacturing a spunbonded non-woven fabric excellent in extensibility is provided.

DESCRIPTION OF EMBODIMENTS

Figure 1A:
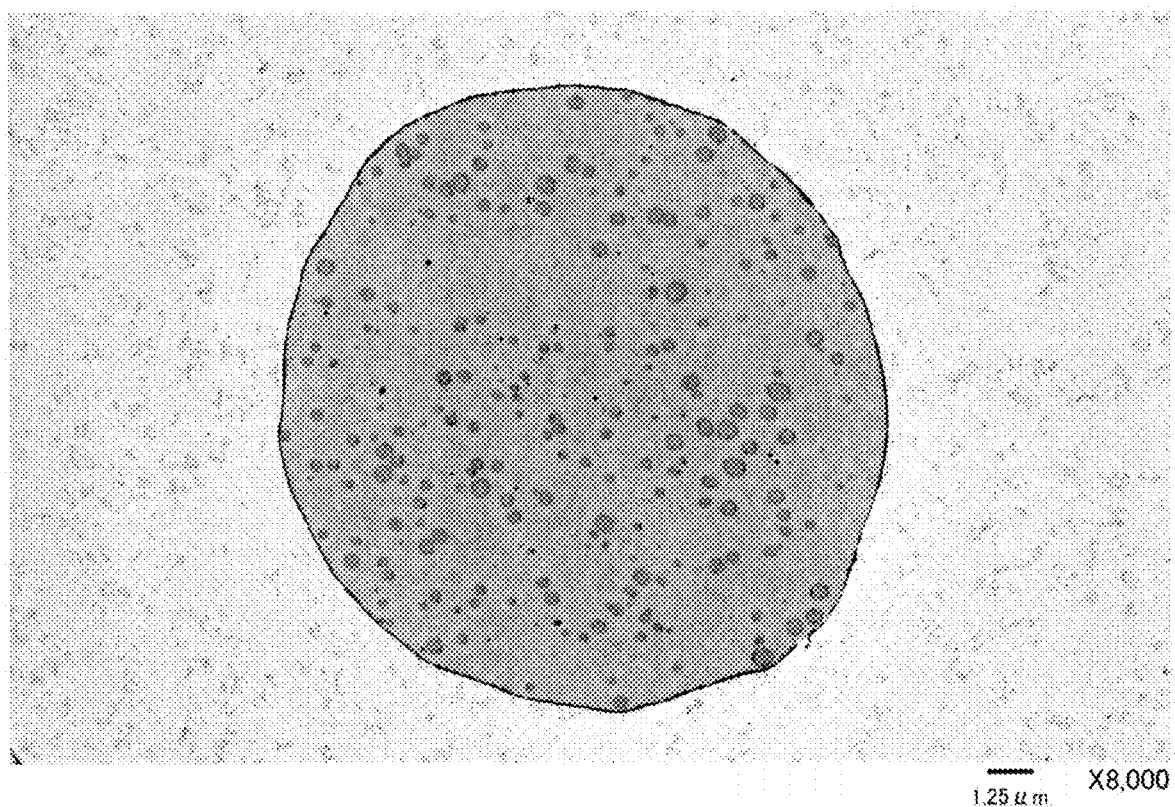
FIG. 1A is an image obtained by observing a cross section of a fiber in a spunbonded non-woven fabric in Example 2, with a transmission electron microscope.

Embodiments of the invention (hereinafter also referred to as "present embodiment") will be described below.

However, the invention is not limited to the following embodiments. In the following embodiments, the constituent elements (including the element steps and the like) are not indispensable except when particularly explicitly mentioned, when it is considered to be obviously indispensable in principle, or the like. The same applies to numerical values and ranges thereof, and does not limit the invention.

In the present specification, the term "step" encompasses not only an independent step but also a step of which the object is achieved even in a case in which the step is incapable of being definitely distinguished from another step.

In the present specification, in a case in which plural kinds of substances corresponding to each constituent are present in a composition, the content of each constituent in the composition means the total amount of the plural kinds of the substances present in the composition unless otherwise specified.

<Spunbonded Non-Woven Fabric>

A spunbonded non-woven fabric of the present embodiment is a spunbonded non-woven fabric including a fiber including a composition including a propylene homopolymer having a melting point of 140° C. or more, a polyethylene having a density of from 0.941 g/cm³ to 0.970 g/cm³, and at least one polymer selected from the group consisting of a polymer represented in (I) as described below and a polymer represented in (II) as described below, wherein the fiber includes a sea-island structure, and the percentage of an island phase having a diameter of from 0.12 μm to less than 0.63 μm with respect to an island phase in a cross section orthogonal to the axis direction of the fiber on a number basis is 30% or more,

[(I) a random copolymer of propylene and at least one selected from ethylene or an α-olefin having a carbon number of from 4 to 20, and (II) a propylene homopolymer with a melting point of less than 120° C., satisfying (a) to (f) as described below, (a) [mmmm]=from 20% by mol to 60% by mol,
(b) [rrrr]/(1−[mmmm])≤0.1,
(c) [rmrm]>2.5% by mol,
(d) [mm]×[rr]/[mr]²≤2.0,
(e) weight-average molecular weight (Mw)=from 10,000 to 200,000, and
(f) molecular weight distribution (Mw/Mn)≤4, wherein in (a) to (d), [mmmm] represents a meso-pentad fraction, [rrrr] represents a racemic pentad fraction, [rmrm] represents a racemic meso-racemic meso-pentad fraction, and [mm], [rr], and [mr] each represent a triad fraction].

"At least one polymer selected from group consisting of polymer represented in (I) and polymer represented in (II)" may be generically referred to as "specific polymer".

The spunbonded non-woven fabric of the present embodiment includes the fiber including the composition including the propylene homopolymer having a comparatively high melting point, the polyethylene, and the specific polymer. In the spunbonded non-woven fabric, the fiber includes a sea-island structure, and the percentage of an island phase having a diameter of from 0.12 μm to less than 0.63 μm with respect to an island phase in a cross section orthogonal to the axis direction of the fiber on a number basis is 30% or more.

The present inventors obtained new findings that the extensibility of such an obtained spunbonded non-woven fabric which includes a fiber including such a sea-island structure as described above, and in which the percentage of an island phase having a diameter of from 0.12 μm to less than 0.63 μm with respect to an island phase in a cross section orthogonal to the axis direction of the fiber on a number basis is 30% or more, is enhanced. It is presumed that orientation crystallization of polypropylene is inhibited to enhance the extensibility because the fiber includes the sea-island structure as described above. It is considered that the orientation crystallization of the polypropylene is more appropriately inhibited to more enhance the extensibility because the percentage of the island phase having a diameter of from 0.12 μm to less than 0.63 μm is within the range described above.

The spunbonded non-woven fabric of the present embodiment includes the fiber including a sea-island structure. The percentage of the island phase having a diameter of from 0.12 μm to less than 0.63 μm with respect to the island phase in the sea-island structure of the fiber on a number basis is 30% or more. The percentage of the island phase having a diameter of from 0.12 μm to less than 0.63 μm with respect to the island phase on a number basis is preferably 40% or more, more preferably 50% or more, and still more preferably 55% or more, from the viewpoint of improvement in extensible.

In the spunbonded non-woven fabric of the present embodiment, the percentage of an island phase having a diameter of 0.63 μm or more with respect to the island phase in the sea-island structure of the fiber on a number basis is preferably 10% or less, from the viewpoint of improvement in extensibility, more preferably 4% or less, and still more preferably 1% or less.

In the spunbonded non-woven fabric of the present embodiment, the percentage of an island phase having a diameter of less than 0.12 μm with respect to the island phase in the sea-island structure of the fiber on a number basis is preferably 70% or less, from the viewpoint of improvement in extensibility, more preferably 60% or less, and still more preferably 45% or less. The lower limit value of the percentage of the island phase having a diameter of less than 0.12 μm may be 5% or more on a number basis.

The percentages of the island phase having a diameter of 0.63 μm or more, the island phase having a diameter of from 0.12 μm to less than 0.63 μm, and the island phase having a diameter of less than 0.12 μm in the sea-island structure of the fiber are measured by, for example, the following method.

A fiber is taken from the spunbonded non-woven fabric, and the fiber is embedded in paraffin to produce a measurement sample. The measurement sample is placed in a microtome so that a blade is parallel to a direction orthogonal to the axis direction of the fiber. The measurement sample is sliced along the direction orthogonal to the axis direction of the fiber. The fiber obtained by the slicing is subjected to carbon reinforcement, and a cross section of the fiber obtained by the slicing is then observed using a transmission electron microscope (TEM). A sea-island pattern is confirmed on the cross section of the fiber. A continuous phase is regarded as a sea phase, and a dispersely existing phase is regarded as an island phase. The diameters of island phases in an observation region (cross section) are measured. The number of island phases having a diameter of 0.63 μm or more, the number of island phases having a diameter of from 0.12 μm to less than 0.63 μm, and the number of island phases having a diameter of less than 0.12 μm were counted. A percentage is calculated by dividing the number of island phases corresponding to each range by the number of the island phases in the observation region (cross section). A transmission electron microscope, model: H-7650, manufactured by Hitachi High-Tech Corporation is used as the transmission electron microscope, and an observation magnification is set at 6000 times or 8000 times. The diameter of such an island phase is determined by performing image analysis by a Mac-View (Mountech Co., Ltd. Co., Ltd.). Specifically, the major and minor diameters of such an island phase are measured, and the average value of the major and minor diameters is regarded as the diameter.

A known method enables confirmation, if appropriate, that the composition included in the spunbonded non-woven fabric of the present embodiment or a fiber including the composition includes each of the constituents.

The meso-pentad fraction [mmmm], racemic pentad fraction [rrrr], racemic meso-racemic meso-pentad fraction [rmrm], and triad fractions [mm], [rr], and [mr] of the propylene homopolymer having a melting point of less than 120° C. in the polymer represented in (II) can be calculated according to a method proposed in "Macromolecules, 6,925 (1973)" by A. Zambelli et al., as described below.

The content of the polyethylene in the composition in the present embodiment is preferably from 1.0% by mass to 15.0% by mass, more preferably from 3.0% by mass to 12.0% by mass, and still more preferably from 6.0% by mass to 10.0% by mass.

The extensibility of the obtained spunbonded non-woven fabric can be improved in a case in which the content of the polyethylene in the composition is in the range described above.

The polyethylene included in the composition in the present embodiment has a density ranging from 0941 g/cm$^3$ to 0.970 g/cm$^3$ in view of improvement in the strength of the spunbonded non-woven fabric.

The strength of the obtained spunbonded non-woven fabric can be improved by allowing the density of the polyethylene in the composition to be in the range described above.

The content of the specific polymer in the composition in the present embodiment is preferably from 5.0% by mass to 30.0% by mass, more preferably from 10.0% by mass to 30.0% by mass, and still more preferably from 15.0% by mass to 25.0% by mass.

The extensibility of the obtained spunbonded non-woven fabric can be improved by allowing the content of the polyethylene in the composition to be in the range described above.

In view of more improving the extensibility of the obtained spunbonded non-woven fabric, the specific polymer in the present embodiment is preferably (I) the random copolymer including at least a constitutional unit derived from propylene and a constitutional unit derived from ethylene, or (II) the propylene homopolymer having a melting point of less than 120° C., satisfying (a) to (f), more preferably the random copolymer including at least a constitutional unit derived from propylene and a constitutional unit derived from ethylene, and still more preferably a random copolymer consisting of a constitutional unit derived from propylene and a constitutional unit derived from ethylene.

In the composition in the present embodiment, the content of the propylene homopolymer having a melting point of 140° C. or more is preferably from 55.0% by mass to 90.0% by mass, more preferably from 60.0% by mass to 85.0% by mass, and still more preferably from 65.0% by mass to 80.0% by mass.

Since the content of the propylene homopolymer having a melting point of 140° C. or more in the composition is in the range described above, the extensibility of the obtained spunbonded non-woven fabric can be improved, the physical property (strength) of the spunbonded non-woven fabric is maintained in a favorable range, and it is easy to obtain the flexible non-woven fabric having a low basis weight.

The composition in the present embodiment preferably includes a fatty acid amide having a carbon number of from 15 to 22. In a case in which the composition includes the fatty acid amide having a carbon number of from 15 to 22, the surfaces of the fibers of the spunbonded non-woven fabric formed with the composition adsorb the fatty acid amide having a carbon number of from 15 to 22, to reform the surfaces of the fibers. As a result, the extensibility and flexibility of the non-woven fabric are more improved.

The content of the fatty acid amide having a carbon number of from 15 to 22 is preferably from 0.1% by mass to 5.0% by mass, more preferably from 0.1% by mass to 3.0% by mass, and still more preferably from 0.1% by mass to 1.0% by mass, with respect to the total amount of the composition.

The spunbonded non-woven fabric of the present embodiment can be manufactured by a usual method using the composition described in detail below.

The basis weight of the spunbonded non-woven fabric of the present embodiment is not particularly limited.

Commonly, the basis weight of the non-woven fabric of the present embodiment is preferably 30 $g/m^2$ or less, more preferably 28 $g/m^2$ or less, still more preferably 25 $g/m^2$ or less, and most preferably in a range of from 5 $g/m^2$ to 20 $g/m^2$, from the viewpoint of achieving both flexibility and strength. In a case in which the spunbonded non-woven fabric of the present embodiment is applied to a sanitary material described below, or the like, the basis weight of the spunbonded non-woven fabric is preferably in a range of from 5 $g/m^2$ to 19 $g/m^2$. The basis weight of the spunbonded non-woven fabric is measured by, for example, the following method.

Ten test pieces of 300 mm in a machine direction (MD) and 250 mm in a cross direction (CD) are collected from a spunbonded non-woven fabric. Places at which the test pieces are collected are set at optional ten places. Then, the mass (g) of each collected test piece is measured using an electronic balance scale (manufactured by KENSEI KOGYO Co., Ltd.). The average value of the masses of the test pieces is determined. The determined average value is converted into a mass (g) per $m^2$, which is rounded off to the nearest whole number, which is regarded as the basis weight [$g/m^2$] of the spunbonded non-woven fabric.

Commonly, a fiber included in a spunbonded non-woven fabric preferably has a fiber diameter of 50 μm or less, more preferably 40 μm or less, still more preferably 30 μm or less, and most preferably 20 μm or less. The smaller the fiber diameter is, the more favorable the flexibility of the non-woven fabric is. The fiber diameter is preferably 10 μm or more from the viewpoint of handleability, production suitability, and inhibition of occurrence of fuzz in the obtained non-woven fabric.

[Physical Properties of Spunbonded Non-Woven Fabric]

The preferred physical properties of the spunbonded non-woven fabric of the present embodiment will be described below.

(Heat-Sealing Property)

One of the physical properties of the spunbonded non-woven fabric of the present embodiment is a heat-sealing property.

In a case in which two non-woven fabrics are put on one another and heat-sealed by a heat sealing test machine, the non-woven fabrics can be preferably heat-sealed at a temperature of 180° C. or less, and more preferably heat-sealed at a temperature of 160° C. or less, for the heat-sealing property of the spunbonded non-woven fabric.

It is preferable to suppress burning in the case of performing heat-sealing under the conditions described above, i.e., discoloration caused by heating.

The tensile peel strength of the two spunbonded non-woven fabrics that have been heat-sealed is set, if appropriate, depending on the purpose of use of the spunbonded non-woven fabrics, and is commonly preferably 0.05 N/20 mm or more, and more preferably 0.1 N/20 mm or more. The tensile peel strength of the spunbonded non-woven fabrics is measured by, for example, the following method.

Ten test pieces of 100 mm in a machine direction (MD) and 100 mm in a cross direction (CD) are collected from a spunbonded non-woven fabric. Then, two of the test pieces are put on one another so that the MD directions of the test pieces are the same. The test pieces are heat-sealed using a heat sealing test machine (product name: HEAT SEAL TESTER), manufactured by TESTER SANGYO CO., LTD., under the following conditions.

Seal bar width: 10.0 mm
Seal pressure: 2.0 $kg/cm^2$
Seal time: 1.0 second
Seal temperature: the temperatures of upper and lower bars are set at the same temperature (145° C., 155° C.)
Seal direction: perpendicular to MD Five test pieces of the test pieces heat-sealed under the conditions described above are subjected to each tensile peel test using a constant-speed tensile testing machine (product name: STROGRAPH, manufactured by Toyo Seiki Seisaku-sho, Ltd.) under the following conditions. The average value of values obtained in the measurement is regarded as tensile peel strength.

Shape of test piece: 20 mm in width, 50 mm in length
Tension speed: 30 mm/min Ambient temperature in measurement: 23° C.

(Embossment Residual Rate)

One of the physical properties of the spunbonded non-woven fabric of the present embodiment is an embossment residual rate.

The embossment residual rate of the spunbonded non-woven fabric after stretching processing of the spunbonded non-woven fabric is preferably 40% or more, more preferably 50% or more, and still more preferably 70% or more.

An embossment residual rate of 40% or more after the stretching processing results in the more favorable texture of the spunbonded non-woven fabric.

The embossment residual rate is measured by, for example, the following method.

Figure 3:
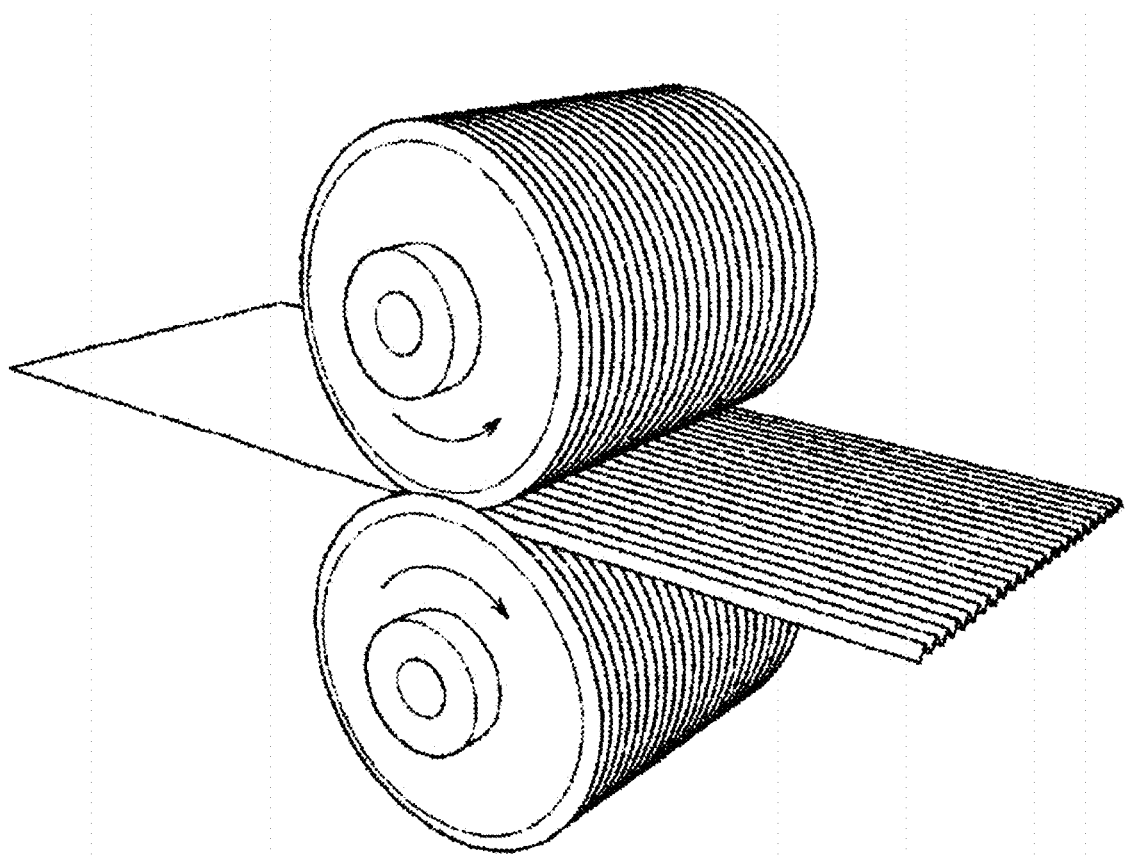
FIG. 3 is a schematic view of a gear stretching apparatus.

One test piece of 250 mm in a machine direction (MD) and 200 mm in a cross direction (CD) is collected from a spunbonded non-woven fabric. The obtained test piece is inserted so that the roll rotation direction of such a gear stretching apparatus (i.e., a gear processing machine) as illustrated in FIG. 3 and the CD direction of the test piece coincide with each other. Thus, a spunbonded non-woven fabric gear-stretched in the MD direction (i.e., the machine direction of the non-woven fabric) is obtained. Gear rolls mounted in the gear processing machine are adjusted so that each of the gear rolls has a diameter of 200 mm and a gear pitch of 2.5 mm, and the depth of mesh between both the rolls is 5.5 mm. The form of the embossed portion of the gear-stretched spunbonded non-woven fabric is observed using a scanning electron microscope (SEM). The embossment residual rate is calculated based on the following equation.

Embossment residual rate=(the number of undamaged embossments/the number of observed embossments)×100

An embossed portion in which none of pitting of the embossed portion, desorption of a fiber, and cutting of a fiber in the embossed portion and the boundary of the embossed portion is confirmed in the observation of the embossed portion of the gear-stretched spunbonded non-woven fabric is regarded as "undamaged embossment". "The number of undamaged embossments" means the number of undamaged embossments present in an observation region. "The number of observed embossments" means the number of embossments present in an observation region. An S-3500N-type scanning electron microscope manufactured by Hitachi, Ltd. is used as the scanning electron microscope, and an observation magnification is set at 100 times.

(Flexibility)

One of the physical properties of the spunbonded non-woven fabric of the present embodiment is flexibility.

The flexibility of a spunbonded non-woven fabric greatly influences the sense of use of the non-woven fabric. Examples of the flexibility include flexibility based on sensory evaluation by touch.

(Maximum Elongation and Maximum Strength)

Examples of the preferred physical properties of the spunbonded non-woven fabric of the present embodiment include maximum elongation and maximum strength.

The spunbonded non-woven fabric of the present embodiment preferably has a maximum elongation, at least one direction, of 70% or more, more preferably 100% or more, and still more preferably 140% or more.

The spunbonded non-woven fabric of the present embodiment preferably has a maximum strength, in at least one direction, of 10 N/50 mm or more, more preferably 15 N/50 mm or more, and still more preferably 20 N/50 mm or more.

The spunbonded non-woven fabric preferably has a property of little elastic recovery.

The maximum elongation and maximum strength of the spunbonded non-woven fabric are measured by, for example, the following method.

Five test pieces of 25 cm in a machine direction (MD) and 5 cm in a cross direction (CD) are collected from a spunbonded non-woven fabric in conformity with JIS L 1906 6.12.1 [Method A] (changed to JIS L 1913: 2010; corresponding to ISO 9073-3: 1989) in a thermostatic chamber at a temperature of 20±2° C. and a humidity of 65±2%, specified in JIS Z 8703 (corresponding to ISO 554: 1976; Standard Atmospheric Conditions for Testing). A tensile test of the obtained test pieces is conducted using a tensile tester (INSTRON 5564 Type, manufactured by Instron Japan Company Limited) under conditions of a spacing between chucks, of 100 mm, and a tension speed of 300 mm/min. The tensile loads of the five test pieces are measured, and the average value of the maximum values of the tensile loads is regarded as the maximum strength.

An elongation at the maximum strength is regarded as the maximum elongation.

The spunbonded non-woven fabric of the present embodiment can be manufactured by a usual method using one or more of compositions described in detail below.

[Composition]

A composition included in the spunbonded non-woven fabric of the present embodiment includes a propylene homopolymer having a melting point of 140° C. or more (hereinafter, may be referred to as "specific polypropylene"), a polyethylene having a density of from 0.941 g/cm$^3$ to 0.970 g/cm$^3$, and at least one polymer (specific polymer) selected from the group consisting of a polymer represented in (I) and a polymer represented in (II), as previously described.

From the viewpoint of effectively achieving the object of the present embodiment, the total content of the specific polypropylene and the specific polymer in the total amount of the composition is preferably 80% by mass or more, more preferably 90% by mass or more, and still more preferably 95% by mass or more.

[Propylene Homopolymer Having Melting Point of 140° C. or More (Specific Polypropylene)]

The propylene homopolymer having a melting point of 140° C. or more includes a constitutional unit derived from propylene, and has a melting point of 140° C. or more.

The melting point of the propylene homopolymer is preferably 150° C. or more.

A resin having a melting point (Tm) of above 140° C., which is a crystalline resin produced or sold under the name of polypropylene, can be used as the specific polypropylene. Examples of such commercially available products include a propylene homopolymer having a melting point of 155° C. or more, preferably in a range of from 157° C. to 165° C.

The melting point of the specific polypropylene is defined as the peak top of a peak observed in the highest-temperature side of a melt endotherm curve obtained, using a differential scanning calorimeter (DSC), by keeping the specific polypropylene under nitrogen atmosphere at −40° C. for 5 minutes and then increasing the temperature of the specific polypropylene at 10° C./min.

Specifically, the melting point can be determined as the peak top of a peak observed in the highest-temperature side of a melt endotherm curve obtained, using a differential scanning calorimeter (DSC-7, manufactured by PerkinElmer, Inc.), by keeping 5 mg of sample under nitrogen atmosphere at −40° C. for 5 minutes and then increasing the temperature of the sample at 10° C./min.

The melt flow rate (MFR: ASTM D 1238, 230° C., load of 2160 g) of the specific polypropylene is not particularly limited as long as the specific polypropylene can be melt-spun. The melt flow rate is commonly in a range of from 1 g/10 min to 1000 g/10 min, preferably from 5 g/10 min to 500 g/10 min, and still more preferably from 10 g/10 min to 100 g/10 min.

In the specific polypropylene, only one composition may be used, or two or more compositions of which the melting points, molecular weights, crystal structures, or the like are different from each other may be used.

The preferred content of the specific polypropylene with respect to the total amount of the composition has been previously described.

[Polyethylene]

Examples of polyethylenes with a density of from 0.941 g/cm$^3$ to 0.970 g/cm$^3$, which can be used in the present embodiment, include an ethylene homopolymer such as high-density polyethylene (so-called HDPE) including a constitutional unit derived from ethylene. Extensibility, flexibility, and breaking strength can be more improved by using high-density polyethylene in the composition.

In the composition, only one polyethylene may be used, or two or more polyethylenes of which the melting points, molecular weights, crystal structures, or the like are different from each other may be used.

The preferred content of the polyethylene with respect to the total amount of the composition has been previously described.

[Specific Polymer]

In the present embodiment, use of the composition including a specific polymer enables very excellent stretching processing suitability to be obtained while maintaining favorable flexibility and extensibility in the obtained spunbonded non-woven fabric.

[Polymer Represented in (I): Random Copolymer of Propylene And at Least One Selected from Ethylene Or α-Olefin Having Carbon Number of from 4 to 20]

The polymer represented in (I) (hereinafter, may be referred to as "polymer (I)") is a random copolymer including a constitutional unit derived from propylene and a constitutional unit derived from at least one olefin selected from ethylene or an α-olefin, having a carbon number of from 4 to 20.

In view of improving flexibility without allowing a feeling of stickiness to occur in the obtained spunbonded non-woven fabric, it is preferable that the polymer (I) is a random copolymer.

The polymer (I) is not particularly limited as long as being a random copolymer including the constitutional units.

Examples of monomers that can copolymerize with propylene include an α-olefin having a carbon number of from 4 to 20, such as ethylene, 1-butene, 1-hexene, 4 methyl-1-pentene, 1-octene, or 4-methyl-1-pentene.

Especially, a monomer that is allowed to copolymerize with propylene is preferably ethylene or an α-olefin having a carbon number of from 4 to 8.

The number of the kinds of the constitutional units derived from an α-olefin, included in the polymer (I), may be only one, or may be two or more.

Preferred examples of the polymer (I) include a propylene/1-butene random copolymer, a propylene/ethylene random copolymer, and propylene/ethylene/1-butene random copolymer.

From the viewpoint of effectively achieving the object of the present embodiment, the total percentage of the constitutional unit derived from propylene and the constitutional unit derived from the olefin other than the propylene in all the constitutional units included in the polymer (I) is preferably 80% by mol or more, more preferably 85% by mol or more, and still more preferably 90% by mol or more.

The polymer (I) preferably has a melting point of 100° C. or more, more preferably 130° C. or more, and still more preferably 150° C. or more.

The melting point of the polymer (I) is defined as the peak top of a peak observed in the highest-temperature side of a melt endotherm curve obtained, using a differential scanning calorimeter (DSC), by keeping the polymer (I) under nitrogen atmosphere at −40° C. for 5 minutes and then increasing the temperature of the polymer (I) at 10° C./min.

Specifically, the melting point can be determined as the peak top of a peak observed in the highest-temperature side of a melt endotherm curve obtained, using a differential scanning calorimeter (DSC-7, manufactured by PerkinElmer, Inc.), by keeping 5 mg of sample under nitrogen atmosphere at −40° C. for 5 minutes and then increasing the temperature of the sample at 10° C./min.

The degree of the crystallinity of the polymer (I) is preferably 15% or less, more preferably 10% or less, and still more preferably 8% or less.

The degree of the crystallinity of the polymer (I) is calculated based on a melting heat curve derived from melting of a main constituent, in a melt endotherm curve obtained, using a differential scanning calorimeter (DSC), by keeping the polymer (I) under nitrogen atmosphere at −40° C. for 5 minutes and then increasing the temperature of the polymer (I) at 10° C./min.

Specifically, the degree of the crystallinity can be determined using the following equation based on a melting heat curve derived from melting of a main constituent, in a melt endotherm curve obtained, using a differential scanning calorimeter (DSC-7, manufactured by PerkinElmer, Inc.), by keeping 5 mg of sample under nitrogen atmosphere at −40° C. for 5 minutes and then increasing the temperature of the sample at 10° C./min.

$$\text{Degree of crystallinity} = (\Delta H / \Delta HO) \times 100 (\%)$$

In the expression, ΔH is the amount (J/g) of melting heat determined based on a melting heat curve derived from melting of a main constituent of an α-olefin copolymer including ethylene and propylene, and ΔHO is the amount (J/g) of melting heat of the perfect crystal of the main constituent. In other words, ΔHO is 293 J/g in a case in which the main constituent in the case of ethylene, while ΔHO is 210 J/g in a case in which the main constituent is propylene.

The polymer (I) preferably has a tensile elasticity, measured by a method in conformity with JIS K 7161 (changed to JIS K 7161-1: 2014; corresponding to ISO 527-1: 2012), of 100 MPa or less, more preferably 40 MPa or less, and still more preferably 25 MPa or less.

Commonly, the melt flow rate (MFR: ASTM D 1238, 230° C., load of 2160 g) of the polymer (I) is preferably in a range of from 1 g/10 min to 100 g/10 min, more preferably in a range of from 5 g/10 min to 100 g/10 min, and still more preferably in a range of from 30 g/10 min to 70 g/10 min, in view of obtaining favorable spinnability and excellent stretching processing suitability.

The ratio between the weight-average molecular weight (Mw) and number-average molecular weight (Mn) of the polymer (I) (Mw/Mn (molecular weight distribution)) is commonly from 1.5 to 5.0. The molecular weight distribution (Mw/Mn) of the polymer (I) is still more preferably from 1.5 to 3.0 in view of obtaining a composite fiber with more favorable spinnability and particularly excellent fiber strength.

Favorable spinnability means that yarn breakage and the fusion of a filament are prevented from occurring in discharging and stretching of the polymer (I) from a spinning nozzle.

Mw and Mn of the polymer (I) can be measured by a known method by GPC (gel permeation chromatography).

The details of the measurement method will be described later.

[Polymer Represented in (II): Propylene Homopolymer Satisfying Following Requirements (a) to (f)]

The polymer represented in (II) (hereinafter, may be referred to as "polymer (II)") is a polymer satisfying the following requirements (a) to (f).

First, the requirements (a) to (f) will be described.

(a) [mmmm]=from 20% by mol to 60% by mol

Occurrence of stickiness is suppressed in a case in which the meso-pentad fraction [mmmm] of the polymer (II) is 20% by mol or more, while the degree of crystallinity is prevented from being excessively increased, and therefore, a favorable elastic recovery property is achieved in a case in which the meso-pentad fraction is 60% by mol or less.

The meso-pentad fraction [mmmm] is preferably from 30% by mol to 50% by mol, and more preferably from 40% by mol to 50% by mol.

The meso-pentad fraction [mmmm], and a racemic pentad fraction [rrrr] and a racemic meso-racemic meso-pentad fraction [rmrm] described later are a meso fraction, a racemic fraction, and a racemic meso-racemic meso fraction, respectively, in a pentad unit in a polypropylene molecular chain, measured based on the signal of a methyl group in a $^{13}$C-NMR spectrum according to a method proposed in "Macromolecules, 6,925 (1973)" by A. Zambelli et al. An increase in meso-pentad fraction [mmmm] results in enhanced stereoregularity. Triad fractions [mm], [rr], and [mr] described later are also calculated by the method.

The $^{13}$C-NMR spectrum can be measured in the following apparatus and conditions according to the belonging of a peak, proposed in "Macromolecules, 8,687 (1975)" by A. Zambelli et al.

Apparatus: JNM-EX400 type $^{13}$C-NMR apparatus manufactured by JEOL Ltd.

Method: Proton complete decoupling method Concentration: 220 mg/mL Solvent: Mixed solvent (90: 10 (volume ratio)) of 1,2,4-trichlorobenzene and heavy benzene Temperature: 130° C.

Pulse width: 45° Pulse recurrence time: 4 sec Integration: 10000 times

[Calculation Expression]

$M=m/S\times 100$ $R=\gamma/S\times 100$ $S=P\beta\beta+P\alpha\beta+P\alpha\gamma$ S: Signal intensity of side-chain methyl carbon atom in all propylene units Pββ: Signal intensity at from 19.8 ppm to 22.5 ppm Pαβ: Signal intensity at from 18.0 ppm to 17.5 ppm Pαγ: Signal intensity at from 17.5 ppm to 17.1 ppm γ: Racemic pentad chain: signal intensity at from 20.7 ppm to 20.3 ppm m: Meso-pentad chain: signal intensity at from 21.7 ppm to 22.5 ppm M represents the abundance rate of a meso-pentad chain in propylene, and R represents the abundance rate of a racemic pentad chain in propylene.

(b) [rrrr]/(1−[mmmm])≤0.1

The value of [rrrr]/[1−mmmm] is determined from the fractions of the racemic pentad unit and the meso-pentad unit, and is an index indicating the uniformity of the regularity distribution of the constitutional unit derived from propylene in the polymer (II). In a case in which the value is increased, a mixture of high-regularity polypropylene and atactic polypropylene, such as conventional polypropylene produced using an existing catalyst type, is generated, thereby causing stickiness.

Stickiness in the obtained spunbonded non-woven fabric is suppressed in a case in which [rrrr]/(1−[mmmm]) is 0.1 or less in the polymer (II). From such a viewpoint, [rrrr]/(1−[mmmm]) is preferably 0.05 or less, and more preferably 0.04 or less.

(c) [rmrm]>2.5% by mol

The randomness of the polymer (II) is increased, and the elastic recovery property of the spunbonded non-woven fabric is further improved, in a case in which the racemic meso-racemic meso fraction [rmrm] of the polymer (II) is a value of more than 2.5% by mol. The value of [rmrm] is preferably 2.6% by mol or more, and more preferably 2.7% by mol or more. Commonly, the upper limit of the racemic meso-racemic meso fraction [rmrm] of the polymer (II) is around 10% by mol.

(d) [mm]×[rr]/[mr]²≤2.0

The value of [mm]×[rr]/[mr]² indicates an index of the randomness of the polymer (II). In the elastic non-woven fabric, a sufficient elastic recovery can be obtained, and stickiness is also suppressed, in a case in which the value is 2.0 or less. The randomness becomes higher in a case in which the value of [mm]×[rr]/[mr]² is closer to 0.25. From the viewpoint of obtaining the sufficient elastic recovery property, the value of [mm]×[rr]/[mr]² is preferably from more than 0.25 to 1.8, and more preferably from 0.5 to 1.5.

(e) Weight-average molecular weight (Mw)=from 10,000 to 200,000

In a case in which the weight-average molecular weight of the polymer (II) which is a propylene homopolymer is 10,000 or more, the viscosity of the polymer (II) is prevented from becoming excessively low and becomes moderate, and therefore, yarn breakage is suppressed in manufacturing of the spunbonded non-woven fabric obtained from the composition. In a case in which the weight-average molecular weight is 200,000 or less, the viscosity of the polymer (II) is prevented from becoming excessively high, whereby spinnability is improved.

The weight-average molecular weight is preferably from 30,000 to 150,000, and more preferably from 50,000 or to 150,000.

A method of measuring the weight-average molecular weight of the polymer (II) will be described later.

(f) Molecular Weight Distribution (Mw/Mn)≤4

Occurrence of stickiness in the obtained spunbonded non-woven fabric is suppressed in a case in which the molecular weight distribution (Mw/Mn) of the polymer (II) is less than 4. The molecular weight distribution is preferably from 1.5 to 3.

The weight-average molecular weight (Mw) is a weight-average molecular weight, in terms of polystyrene, measured by a gel permeation chromatography (GPC) method in the following apparatus and conditions. The molecular weight distribution (Mw/Mn) is a value calculated based on a number-average molecular weight (Mn) measured in a similar manner and the weight-average molecular weight (Mw).

[GPC Measurement Apparatus]

Column: TOSO GMHHR-H (S) HT

Detection instrument: RI detection instrument for liquid chromatogram: WATERS 150C

[Measurement condition]

Solvent: 1,2,4-Trichlorobenzene

Measured temperature: 145° C.

Flow rate: 1.0 mL/min

Concentration of sample: 2.2 mg/mL

Injection amount: 160 μL

Calibration curve: Universal Calibration

Analysis program: HT-GPC (Ver.1.0)

It is preferable that the polymer (II) further satisfies the following requirement (g).

(g) Melting point (Tm–D)=from 0° C. to 120° C.

The melting point (Tm–D) of the polymer (II) is (g) a melting point (Tm–D) defined as the peak top of a peak observed in the highest-temperature side of a melt endotherm curve obtained, using a differential scanning calorimeter (DSC), by keeping the polymer (II) under nitrogen atmosphere at −10° C. for 5 minutes and then increasing the temperature of the polymer (II) at 10° C./min.

Occurrence of stickiness in the spunbonded non-woven fabric formed with the composition is suppressed in a case in which the melting point (Tm–D) of the polymer (II) is 0° C. or more, while a sufficient elastic recovery property can be obtained in a case in which the melting point (Tm–D) is 120° C. or less. From such a viewpoint, the melting point (Tm–D) is more preferably from 0° C. to 100° C., and still more preferably from 30° C. to 100° C.

The melting point (Tm–D) can be determined as the peak top of a peak observed in the highest-temperature side of a melt endotherm curve obtained, using a differential scanning calorimeter (DSC-7, manufactured by PerkinElmer, Inc.), by keeping 10 mg of sample under nitrogen atmosphere at −10° C. for 5 minutes and then increasing the temperature of the sample at 10° C./min.

Commonly, the melt flow rate (MFR: ASTM D 1238, 230° C., load of 2160 g) of the polymer (II) is preferably in a range of from 1 g/10 min to 100 g/10 min, more preferably in a range of from 5 g/10 min to 100 g/10 min, and still more preferably in a range of from 30 g/10 min to 70 g/10 min, in view of obtaining favorable spinnability and excellent stretching processing suitability.

The polymer (II) can be synthesized using, for example, such a homogeneous catalyst, referred to as so-called "metallocene catalyst", as described in International Publication NO. WO 2003/087172.

[Additive]

The composition may include various known additives such as an antioxidant, a heat stabilizer, a weathering stabilizer, an antistatic agent, a slipping agent, an antifogging agent, a lubricant, a dye, a pigment, a natural oil, a synthetic oil, a wax, and a fatty acid amide, as optional constituents, as long as the object of the present embodiment is met.

[Fatty Acid Amide]

The composition preferably includes a fatty acid amide having a carbon number of from 15 to 22, as previously described.

It is conceivable that in a case in which the composition includes the fatty acid amide, the surfaces of the fibers of the spunbonded non-woven fabric formed with the composition adsorb the fatty acid amide, to reform the surfaces of the fibers to more improve flexibility, texture, blocking resistance, and the like, whereby adhesion of the non-woven fabric fibers to the members of various rotation instruments and the like in an apparatus used in an embossment step and the like is more effectively suppressed.

Examples of the fatty acid amide having a carbon number of from 15 to 22 include a fatty acid monoamide compound, a fatty acid diamide compound, a saturated fatty acid monoamide compound, and unsaturated fatty acid diamide compound.

The carbon number of the fatty acid amide in the present specification means the number of carbon atoms included in the molecule. The carbon number also includes the number of the carbon atom in —CONH included in the amide. The carbon number of the fatty acid amide is more preferably from 18 to 22.

Specific examples of the fatty acid amide that can be used in the composition include a palmitic acid amide (carbon number of 16), a stearic acid amide (carbon number of 18), an oleic acid amide (carbon number of 18), and an erucic acid amide (carbon number of 22).

In the composition, only one fatty acid amide may be used, or two or more fatty acid amides may be used.

The preferred content of the fatty acid amide with respect to the total amount of the composition has been previously described.

<Method of Manufacturing Spunbonded Non-Woven Fabric>

The spunbonded non-woven fabric of the present embodiment can be manufactured by a usual method using one or more of the previously described compositions.

Specifically, the spunbonded non-woven fabric of the present embodiment is preferably manufactured by a method of manufacturing a spunbonded non-woven fabric of the present embodiment, described below.

The method of manufacturing a spunbonded non-woven fabric of the present embodiment includes extruding a composition including a propylene homopolymer having a melting point of 140° C. or more, a polyethylene having a density of from 0.941 g/cm$^3$ to 0.970 g/cm$^3$, and a specific polymer, from an extruding machine A and an extruding machine B so that the amounts of the composition extruded from the extruding machine A and the extruding machine B, respectively, achieve from 85:15 to 55:45 (extruding machine A: extruding machine B) on a mass basis.

The inventors obtained new findings that the extensibility of an obtained spunbonded non-woven fabric is enhanced by extruding a resin composition at different percentages from two extruding machines, as described above. It is conceivable that the orientation crystallization of polypropylene is more appropriately is inhibited to more enhance extensibility by extruding a resin composition at different percentage from two extruding machines, as described above.

In the method of manufacturing a spunbonded non-woven fabric of the present embodiment, the extensibility of a spunbonded non-woven fabric can be improved by using the two extruding machines, which are the extruding machine A and the extruding machine B.

From the viewpoint of improving the extensibility of the spunbonded non-woven fabric, the amounts of the composition extruded from the extruding machine A and the extruding machine B, respectively, preferably achieve from 80:20 to 55:45, and more preferably from 75:25 to 55:45.

The method of manufacturing a spunbonded non-woven fabric of the present embodiment preferably includes mixing the same composition in each extruding machine (hereinafter also referred to as "mixing step"), and supplying the same composition, melted through the mixing step, from the extruding machine A and the extruding machine B to nozzles. Melted resins that have exited from the extruding machine A and the extruding machine B become confluent before arriving at a spinneret, and twisted yarn is molded in a non-woven fabric formation step in which a non-woven fabric is obtained by a spunbonding method.

The bore A of the extruding machine A of the present embodiment is preferably larger than the bore B of the extruding machine B from the viewpoint of improving the extensibility of the spunbonded non-woven fabric.

The bore means the bore of a flow path connected to the outlet portion of extruding machine (hereinafter also referred to as "extruder"), i.e., the nozzle. The shape of the spinneret of the extruding machine is not particularly limited.

[Mixing Step]

In the mixing step, the composition is obtained by mixing a propylene homopolymer having a melting point of 140° C. or more, a polyethylene having a density of from 0.941 g/cm$^3$ to 0.970 g/cm$^3$, and a specific polymer.

Each of the constituents other than the polyethylene, i.e., the propylene homopolymer having a melting point of 140° C. or more, the specific polymer, and an additive (an optional constituent such as a fatty acid amide having a carbon number of from 15 to 22), used in this step, may be in a molten state, or may be solid.

This step may be performed in the extruders used in the non-woven fabric formation step.

The content of the polyethylene used in this step is preferably from 1.0% by mass to 15.0% by mass with respect to the total amount of the composition.

The content of the specific polymer used in this step is preferably from 5% by mass to 30% by mass with respect to the total amount of the composition.

The content of the propylene homopolymer having a melting point of 140° C. or more, used in this step, is preferably from 55.0% by mass to 90.0% by mass with respect to the total amount of the composition.

This step is preferably a step in which a fatty acid amide having a carbon number of from 15 to 22 is further mixed to obtain the composition.

In other words, this step is preferably a step in which the propylene homopolymer having a melting point of 140° C. or more, the polyethylene having a density of from 0.941 g/cm$^3$ to 0.970 g/cm$^3$, the specific polymer, and the fatty acid amide having a carbon number of from 15 to 22 are mixed to obtain the composition.

The content of the fatty acid amide having a carbon number of from 15 to 22, used in this step, is preferably from 0.1% by mass to 5.0% by mass with respect to the total amount of the composition.

[Non-Woven Fabric Formation Step]

In the non-woven fabric formation step, the non-woven fabric is obtained, from the composition obtained in the mixing step, by a spunbonding method.

In this step, the non-woven fabric is obtained by, for example, the following method.

In other words, the method is a method in which the same composition is melted using the two extruders, the same melted composition is melt-spun using a spunbonded non-woven fabric molding machine including plural spinnerets, and long fibers formed by spinning are cooled, if necessary, then deposited on the collection surface of the spunbonded non-woven fabric molding machine, and subjected to heating and pressurization treatment by an embossing roll.

The melt temperature of the composition is not particularly limited as long as being not less than the softening temperature or melting temperature of the composition used in the spinning, and less than the thermal decomposition temperature of the composition. The melt temperature may be determined, if appropriate, depending on the physical properties of the composition used.

The temperature of the spinneret depends on the composition used. Since the composition used in this step is a composition in which the content of the propylene homopolymer is large, the temperatures are preferably from 180° C. to 240° C., more preferably from 190° C. to 230° C., and still more preferably from 200° C. to 225° C.

A technique in which cooling air is blown on the long fibers so that the long fibers are stretched while cooling the long fibers is preferably used in the case of cooling the spun long fibers.

The temperature of the cooling air that cools the spun long fibers is not particularly limited as long as being a temperature at which the composition is solidified. Commonly, the temperature of the cooling air is preferably from 5° C. to 50° C., more preferably from 10° C. to 40° C., and still more preferably in a range of from 15° C. to 30° C.

In a case in which the spun long fibers are stretched by cooling air, the air velocity of the cooling air is commonly in a range of from 100 m/min to 10,000 m/min, and preferably from 500 m/min to 10,000 m/min.

[Non-Woven Fabric Layered Body]

The spunbonded non-woven fabric of the present embodiment may be used singly. Alternatively, depending on a purpose, a non-woven fabric layered body may be formed by layering the spunbonded non-woven fabric of the present embodiment and another layer, or a non-woven fabric layered body including the plural spunbonded non-woven fabrics of the present embodiment may be formed.

In a case in which a non-woven fabric layered body is formed using the spunbonded non-woven fabric of the present embodiment, the number of layers other than the spunbonded non-woven fabric of the present embodiment may be one or more.

Specific examples of the layers other than the spunbonded non-woven fabric of the present embodiment include knitted fabrics, woven fabrics, non-woven fabrics other than the spunbonded non-woven fabric of the present embodiment, and films.

A method in which another layer is layered on (affixed to) the spunbonded non-woven fabric of the present embodiment is not particularly limited. Various methods such as thermal fusion methods such as hot embossing and ultrasonic wave fusion, mechanical entanglement methods such as a needle punch and water jet, methods using adhesives such as hot-melt adhesives and urethane-based adhesives, and extrusion lamination can be adopted as the method.

Examples of another non-woven fabric layered with the spunbonded non-woven fabric of the present embodiment to enable the formation of the non-woven fabric layered body include various known non-woven fabrics such as spunbonded non-woven fabrics other than the spunbonded non-woven fabric of the present embodiment, melt-blown non-woven fabrics, wet-laid non-woven fabrics, dry-laid non-woven fabrics, air-laid pulp non-woven fabrics, flash-spun non-woven fabrics, and open non-woven fabrics.

These non-woven fabrics may be stretchable non-woven fabrics or unstretchable non-woven fabrics.

The unstretchable non-woven fabric refers to a non-woven fabric that does not generate recovery stress after stretching of the non-woven fabric in MD (i.e., the machine direction of the non-woven fabric (lengthwise direction)) or CD (i.e., a direction orthogonal to the machine direction of the non-woven fabric (cross direction)).

In a case in which the non-woven fabric layered body requires air permeability, an air-permeable film, i.e., a moisture-vapor-permeable film is preferred as a film layered with the spunbonded non-woven fabric of the present disclosure to enable the formation of the non-woven fabric layered body.

Examples of the air-permeable film include various known air-permeable films such as a film including a thermoplastic elastomer such as a polyurethane-based elastomer, a polyester-based elastomer, or a polyamide-based elastomer, having moisture vapor permeability, and a porous film formed by stretching a film including a thermoplastic resin including inorganic particles or organic particles and allowing the film to be porous.

Preferred examples of the thermoplastic resin used in the porous film include polyolefins such as high-pressure low-density polyethylenes, linear low-density polyethylenes (so-called LLDPEs), high-density polyethylenes, polypropylenes, polypropylene random copolymers, and combinations thereof.

In a case in which the non-woven fabric layered body does not require air permeability, a film including one or more thermoplastic resins selected from a polyethylene or a polypropylene can be used.

Examples of a thermal fusion method in the case of thermally fusing a part of the non-woven fabric layered body include various known methods such as a method using means such as ultrasonic waves, hot embossing using an embossing roll, and hot air through.

Especially, it is preferable that the thermal fusion method is hot embossing, because the long fibers are efficiently stretched in the case of stretching the non-woven fabric layered body.

Commonly, an emboss area rate is from 5% to 30%, and preferably from 5% to 20%, and a non-emboss unit area is 0.5 mm² or more, and preferably in a range of from 4 mm² to 40 mm², in a case in which a part of the non-woven fabric layered body is thermally fused by the hot embossing.

The non-emboss unit area is the maximum area of a quadrangle inscribed in embossments, in a non-embossed portion in a minimum unit, of which all the sides are surrounded by embossed portions. Examples of mark shapes include circular, oval, elliptical, square, rhombic, rectangular, and quadrangular shapes, and continuous shapes based on the shapes.

A stretchable non-woven fabric layered body having stretchability can be formed by stretching the obtained non-woven fabric layered body.

A stretching processing method is not particularly limited, and a conventionally known method can be applied as the method.

The stretching processing method may be a partly stretching method, or may be an overall stretching method. The stretching processing method may be a monoaxial stretching method, or may be a biaxial stretching method.

Examples of a method of stretching in a machine direction (MD) include a method of passing a partly fused fiber blend through two or more nip rolls. In such a case, the partly fused non-woven fabric layered body can be stretched by increasing the rotation speed of each of the nip rolls in order of the machine direction. Gear stretching processing can be performed using a gear stretching apparatus.

A stretching rate is preferably 50% or more, more preferably 100% or more, and still more preferably 200% or more, and preferably 1000% or less, and more preferably 400% or less.

In the case of monoaxial stretching, a stretching rate in either a machine direction (MD) or a direction (CD) perpendicular to the machine direction preferably satisfies the stretching rate. In the case of biaxial stretching, at least one of a machine direction (MD) or a direction (CD) perpendicular to the machine direction preferably satisfies the stretching rate.

Stretching processing at such a stretching rate causes stretching of long fibers with elasticity in the spunbonded non-woven fabric, and allows long fibers without stretch- ability to be plastically deformed to stretch the long fibers according to the stretching rate.

Similarly, in other layered layers, a layer having elasticity is elastically deformed, and a layer without elasticity is plastically deformed.

In a case in which a layer with elasticity and a layer without elasticity are layered one on another, and stretched, and stress is then released in the case of forming a non-woven fabric layered body, the layer with elasticity (specifically, long fibers included in the layer) recovers elasticity, and long fibers without elasticity bend repeatedly so as to form folds without recovering elasticity. Thus, the non-woven fabric layered body is enabled to express bulky feeling. Since the plastically deformed long fibers become thin, flexibility and texture can be improved, and a stretch inhibition function can be applied to the non-woven fabric layered body.

<Applications>

The spunbonded non-woven fabric of the present embodiment can be preferably used in, for example, a sanitary material. Examples of the sanitary material include: absorbent articles such as paper diapers and sanitary napkins; medical sanitary materials such as wrappers, medical gauze, face cloths, medical gowns, surgical drapes, and wound dressings; and sanitary masks.

The spunbonded non-woven fabric of the present embodiment can also be preferably used as a cosmetic material such as, for example, a cosmetic face mask or a powder puff.

The spunbonded non-woven fabric of the present embodiment can also be preferably used as an industrial material of which representative examples include filters, sound absorption materials, and oil absorption materials.

The non-woven fabric having excellent extensibility easily gives soft touch, and is therefore suitable in applications of contacting with the skin. Therefore, the non-woven fabric can be more preferably used in sanitary materials in the applications.

In a case in which the spunbonded non-woven fabric of the present embodiment is used in the applications described above, the spunbonded non-woven fabric of the present embodiment may be used in a single layer, the spunbonded non-woven fabrics of the present embodiment may be layered and used, or the spunbonded non-woven fabric of the present embodiment and another laminar article may be layered and used. In other words, the spunbonded non-woven fabric of the present embodiment may be used as a non-woven fabric layered body including the spunbonded non-woven fabric of the present embodiment. Examples of the other laminar article include non-woven fabrics other than the spunbonded non-woven fabric of the present embodiment, films, cottons, and felts.

<Sanitary Material>

A sanitary material of the present embodiment includes the previously described spunbonded non-woven fabric of the present embodiment.

The spunbonded non-woven fabric of the invention is excellent in extensibility. Therefore, the spunbonded non-woven fabric of the present embodiment is preferably used in the sanitary material.

The sanitary material may include the spunbonded non-woven fabric of the present embodiment as a non-woven fabric layered body including the spunbonded non-woven fabric of the present embodiment and another layer.

EXAMPLES

Embodiments of the invention will be further specifically described below. However, the invention is not limited to these examples of which each is one embodiment of the invention.

Physical property values and the like in Examples and Comparative Example were measured by the following methods.

(1) Diameter [μm] of Island Phase

A fiber was taken from a spunbonded non-woven fabric, and the fiber was embedded in paraffin to produce a measurement sample. The measurement sample was placed in a microtome so that a blade was parallel to a direction orthogonal to the axis direction of the fiber. The measurement sample was sliced along the direction orthogonal to the axis direction of the fiber. Then, the fiber obtained by the slicing was subjected to carbon reinforcement, and a cross section of the fiber obtained by the slicing was then observed using a transmission electron microscope (TEM). A sea-island pattern was confirmed on the cross section of the fiber. A continuous phase was regarded as a sea phase, and a dispersedly existing phase was regarded as an island phase. The diameters of island phases in an observation region (cross section) were measured. The number of island phases having a diameter of 0.63 μm or more, the number of island phases having a diameter of from 0.12 μm to less than 0.63 μm, and the number of island phases having a diameter of less than 0.12 μm were counted. A percentage was calculated by dividing the number of island phases corresponding to each range by the number of the island phases in the observation region (cross section).

A transmission electron microscope, model: H-7650, manufactured by Hitachi

High-Tech Corporation was used as the transmission electron microscope. An observation magnification was set at 6000 times or 8000 times.

The diameter of such an island phase was determined by performing image analysis by a Mac-View (Mountech Co., Ltd. Co., Ltd.). Specifically, the major and minor diameters of such an island phase were measured, and the average value of the major and minor diameters was regarded as the diameter.

(2) Basis Weight [g/m$^2$]

Ten test pieces of 300 mm in a machine direction (MD) and 250 mm in a cross direction (CD) were collected from the spunbonded non-woven fabric. Places at which the test pieces were collected were set at optional ten places. Then, the mass (g) of each collected test piece was measured using an electronic balance scale (manufactured by KENSEI KOGYO Co., Ltd.). The average value of the masses of the test pieces was determined. The determined average value was converted into a mass (g) per m$^2$, which was rounded off to the nearest whole number, which was regarded as the basis weight [g/m$^2$] of the spunbonded non-woven fabric.

(3) Maximum Elongation [%] and Maximum Strength [N/50 mm]

Five test pieces of 25 cm in a machine direction (MD) and 5 cm in a cross direction (CD) were collected from the spunbonded non-woven fabric in conformity with JIS L 1906 6.12.1 [Method A] (changed to JIS L 1913: 2010; corresponding to ISO 9073-3: 1989) in a thermostatic chamber at a temperature of 20±2° C. and a humidity of 65±2%, specified in JIS Z 8703 (corresponding to ISO 554: 1976; Standard Atmospheric Conditions for Testing). A tensile test of the obtained test pieces was conducted using a tensile tester (INSTRON 5564 Type, manufactured by Instron Japan Company Limited) under conditions of a spacing between chucks, of 100 mm, and a tension speed of 300 mm/min. The tensile loads of the five test pieces were measured, and the average value of the maximum values of the tensile loads was regarded as the maximum strength.

An elongation at the maximum strength was regarded as the maximum elongation.

(4) Evaluation of Heat-Sealing Property

[Heat Sealing Method]

Ten test pieces of 100 mm in a machine direction (MD) and 100 mm in a cross direction (CD) were collected from the spunbonded non-woven fabric. Then, two of the test pieces were put on one another so that the MD directions of the test pieces were the same. The test pieces were heat-sealed using a heat sealing test machine (product name: HEAT SEAL TESTER), manufactured by TESTER SANGYO CO., LTD., under the following conditions.

Seal bar width: 10.0 mm
Seal pressure: 2.0 kg/cm'
Seal time: 1.0 second
Seal temperature: the temperatures of upper and lower bars were set at the same temperature (145° C.)
Seal Direction: Perpendicular to MD

[Confirmation of Heat-Sealing Property]

Five test pieces of the test pieces heat-sealed under the conditions described above were subjected to each tensile peel test using a constant-speed tensile testing machine (product name: STROGRAPH, manufactured by Toyo Seiki Seisaku-sho, Ltd.) under the following conditions. It was confirmed whether or not peeling occurred. A case in which peeling did not occur in all the five pieces was evaluated as "heat-sealing property is present".

Shape of test piece: 20 mm in width, 50 mm in length
Tension speed: 30 mm/min Ambient temperature in measurement: 23° C.

(5) Embossment Residual Rate [%]

One test piece of 250 mm in a machine direction (MD) and 200 mm in a cross direction (CD) was collected from the spunbonded non-woven fabric. The obtained test piece was inserted so that the roll rotation direction of such a gear stretching apparatus (i.e., a gear processing machine) as illustrated in FIG. 3 and the CD direction of the test piece coincided with each other. Thus, a spunbonded non-woven fabric gear-stretched in the MD direction (i.e., the machine direction of the non-woven fabric) was obtained. Gear rolls mounted in the gear processing machine were adjusted so that each of the gear rolls had a diameter of 200 mm and a gear pitch of 2.5 mm, and the depth of mesh between both the rolls was 5.5 mm.

The form of the embossed portion of the gear-stretched spunbonded non-woven fabric was observed using a scanning electron microscope (SEM), and the residual rate of embossments after the gear-stretching was evaluated. It was considered that the higher the embossment residual rate was, the more favorable the texture was. The embossment residual rate was calculated based on the following equation.

$$\text{Embossment residual rate} = (\text{the number of undamaged embossments}/\text{the number of observed embossments}) \times 100$$

An embossed portion in which none of pitting of the embossed portion, desorption of a fiber, and cutting of a fiber in the embossed portion and the boundary of the embossed portion was confirmed in the observation of the embossed portion of the gear-stretched spunbonded non-woven fabric was regarded as "undamaged embossment". "The number of undamaged embossments" means the number of undamaged embossments present in an observation region. "The number of observed embossments" means the number of embossments present in an observation region.

The favorable stretching processing suitability of the spunbonded non-woven fabric can be confirmed in a case in which the residual rate of embossments formed by stretching processing using a gear processing machine is favorable, and none of cutting of the fibers of the spunbonded non-woven fabric in the embossed portion and the boundary of the embossed portion, and breakage of the non-woven fabric, caused by the cutting of the fibers, occurs in the stretching processing.

An S-3500N-type scanning electron microscope manufactured by Hitachi, Ltd. was used as the scanning electron microscope, and an observation magnification was set at 100 times.

(6) Evaluation of Flexibility

For the spunbonded non-woven fabric, sensory evaluation of the texture (touch) of the spunbonded non-woven fabric in a case in which the spunbonded non-woven fabric was directly touched with a hand was conducted based on the following criteria. The sensory evaluation was conducted for ten monitors, and the evaluation result from answers of which the number was the largest was adopted.

In a case in which there were plural evaluation results from answers of which the number was the largest, the most favorable result was adopted.

—Evaluation Criteria—

A: The spunbonded non-woven fabric felt very favorable to the touch, and was excellent in flexibility B: The spunbonded non-woven fabric felt favorable to the touch, and was superior in flexibility to that in the following Evaluation C.

C: The spunbonded non-woven fabric felt solid to the touch, and was poor in flexibility.

Example 1

<Manufacture of Spunbonded Non-Woven Fabric>
—Mixing Step—

A composition was obtained by mixing 7 parts by mass of a high-density polyethylene having an MFR (ASTM D 1238, 230° C., load of 2160 g) of 5 g/10 min, a density of 0.95 g/cm$^3$, and a melting point of 134° C., 72.7 parts by mass of a propylene homopolymer having an MFR (ASTM D 1238, 230° C., load of 2160 g) of 60 g/10 min, a density of 0.91 g/cm$^3$, and a melting point of 160° C., 20 parts by mass of a propylene random copolymer having an MFR (ASTM D 1238, 230° C., load of 2160 g) of 60 g/10 min, a density of 0.91 g/cm$^3$, and a melting point of 142° C. (copolymer of propylene and ethylene, polymerization molar ratio of 97:3, polymer (I)), and 0.3% by mass of erucic acid amide.

—Non-Woven Fabric Formation Step—

Figure 2:
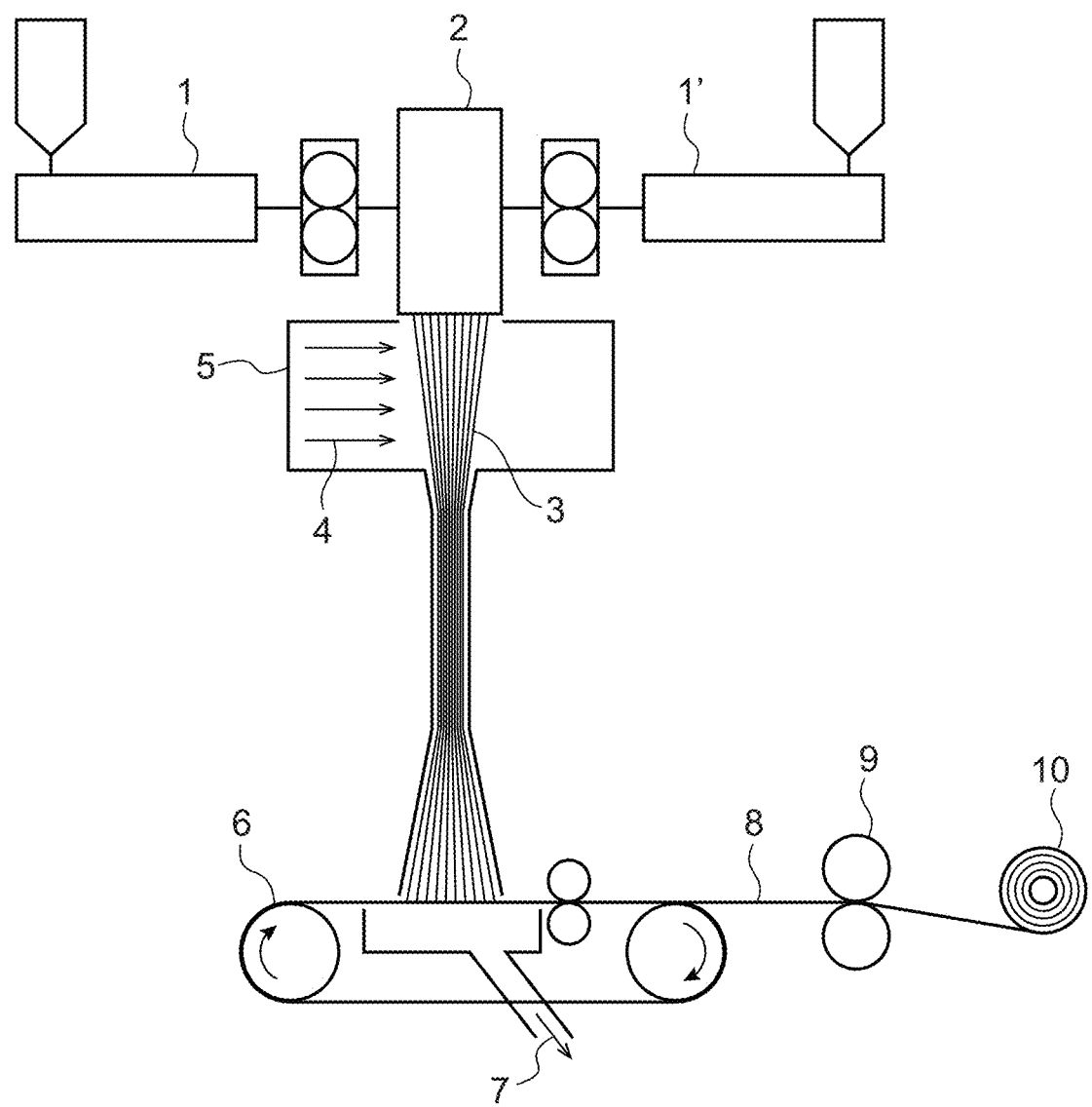
FIG. 2 is a schematic view illustrating an example of a spunbonded non-woven fabric manufacturing apparatus for manufacturing a spunbonded non-woven fabric of the invention.

The composition obtained in the mixing step was melt-spun using a spunbonded non-woven fabric manufacturing apparatus (hereinafter also referred to as "BC") including two extruders illustrated in FIG. 2. The spunbonding manufacturing apparatus includes: an extruder 1 (also referred to as "extruding machine A") and an extruder 1' (also referred to as "extruding machine B") that extrude a source material; a spinneret 2 that spins the extruded source material to form fibers 3; a collector apparatus including a collection surface 6 that traps the stretched fibers to thereby form a non-woven fabric 8; bonding units 9 that thermally fuse at least a part of the non-woven fabric 8; and a winder 10 that winding the thermally fused non-woven fabric. The collector apparatus includes a suction unit 7 for efficiently performing complementary collection of fibers by sucking, below a surface (collection surface 6) on which the fibers are trapped. In the spunbonded non-woven fabric manufacturing apparatus, the fibers 3 obtained through the spinneret 2 are cooled by quenching air 4 (air) in a cooling chamber 5.

Specifically, the melting was performed using the extruder 1 having a bore of 175 mm φ and the extruder 1' having a bore of 150 mm φ, and the melt-spinning was performed by a closed spunbonding method using the spunbonded non-woven fabric manufacturing apparatus (the apparatus used in a closed spunbonding method, having a length of 4273 mm in a direction perpendicular to a machine direction on the collection surface 6) including the spinneret 2 of which the number of the holes was 5776 holes/m under conditions of both a melt temperature of the composition and a die temperature of 240° C., a cooling air temperature of 20° C., and a stretching air quantity of 23653 m$^3$/h. In such a case, the amount of the resin composition extruded from the extruder 1 and the extruder 1' was set at 60:40 on a mass basis.

The spun fibers 3 were deposited on the collection surface 6, and subjected to heating and pressurization treatment (at an emboss area rate (thermocompression bonding rate) of 18% and an embossment temperature of from 125° C. to 130° C.) by embossing rolls to produce the spunbonded non-woven fabric 8 having a total basis weight of 18.0 g/m$^2$.

The obtained spunbonded non-woven fabric in Example 1 was evaluated by the previously described evaluation method.

The results are set forth in Table 1 described below.

Example 2

<Manufacture of Spunbonded Non-Woven Fabric>

An operation similar to the operation of Example 1 was performed except that the amount of resin composition extruded by an extruder 1 and an extruder 1' was set at 70:30 on a mass basis.

An obtained spunbonded non-woven fabric in Example 2 was evaluated by the previously described evaluation method.

The results are set forth in Table 1 described below.

An image obtained by observing a cross section of a fiber in the spunbonded non-woven fabric obtained in Example 2, with a transmission electron microscope, is illustrated in FIG. 1A.

Example 3

<Manufacture of Spunbonded Non-Woven Fabric>

An operation similar to the operation of Example 1 was performed except that the amount of resin composition extruded by an extruder 1 and an extruder 1' was set at 80:20 on a mass basis.

An obtained spunbonded non-woven fabric in Example 3 was evaluated by the previously described evaluation method.

The results are set forth in Table 1 described below.

Figure 1B:
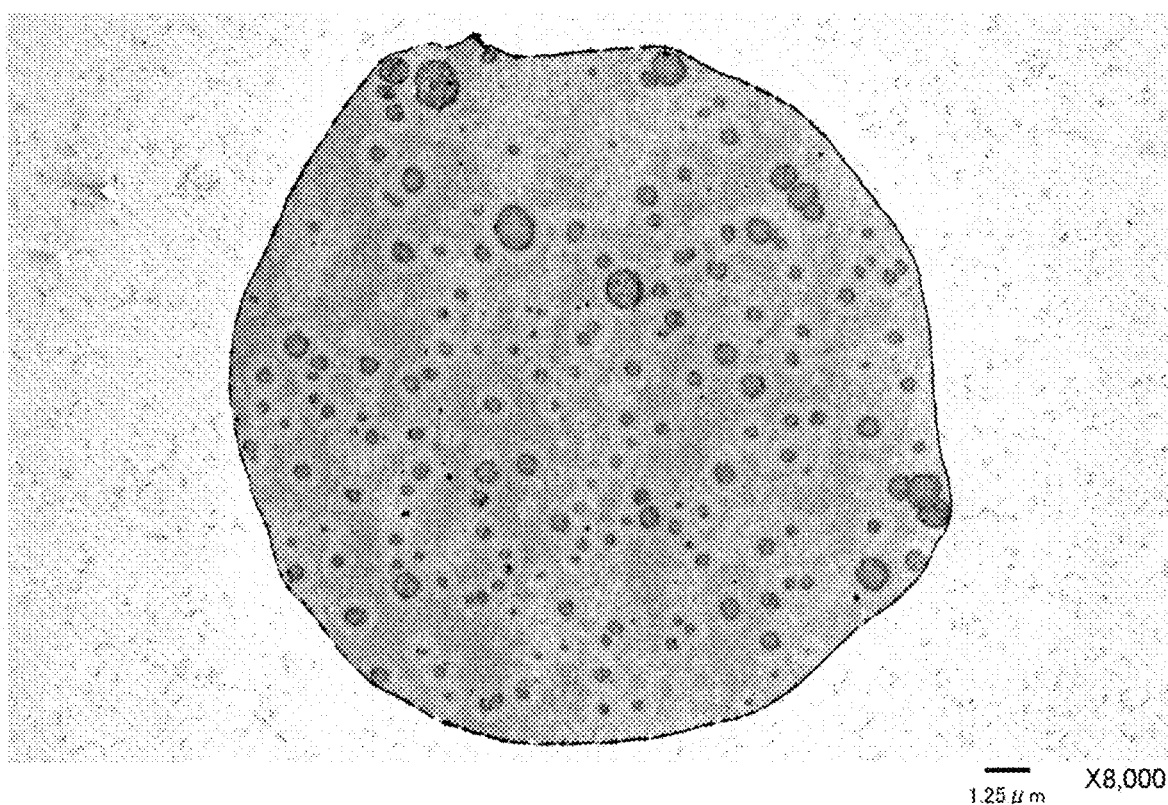
FIG. 1B is an image obtained by observing a cross section of a fiber in a spunbonded non-woven fabric in Example 3, with a transmission electron microscope.

An image obtained by observing a cross section of a fiber in the spunbonded non-woven fabric obtained in Example 3, with a transmission electron microscope, is illustrated in FIG. 1B.

Comparative Example 1

<Manufacture of Spunbonded Non-Woven Fabric>

An operation similar to the operation of Example 1 was performed except that the composition obtained in the mixing step was melt-spun using a spunbonded non-woven fabric manufacturing apparatus (hereinafter also referred to as "MC") including one extruder (not illustrated) instead of the spunbonded non-woven fabric manufacturing apparatus including the two extruders, illustrated in FIG. 2.

An obtained spunbonded non-woven fabric in Comparative Example 1 was evaluated by the previously described evaluation method.

The results are set forth in Table 1 described below.

Figure 1C:
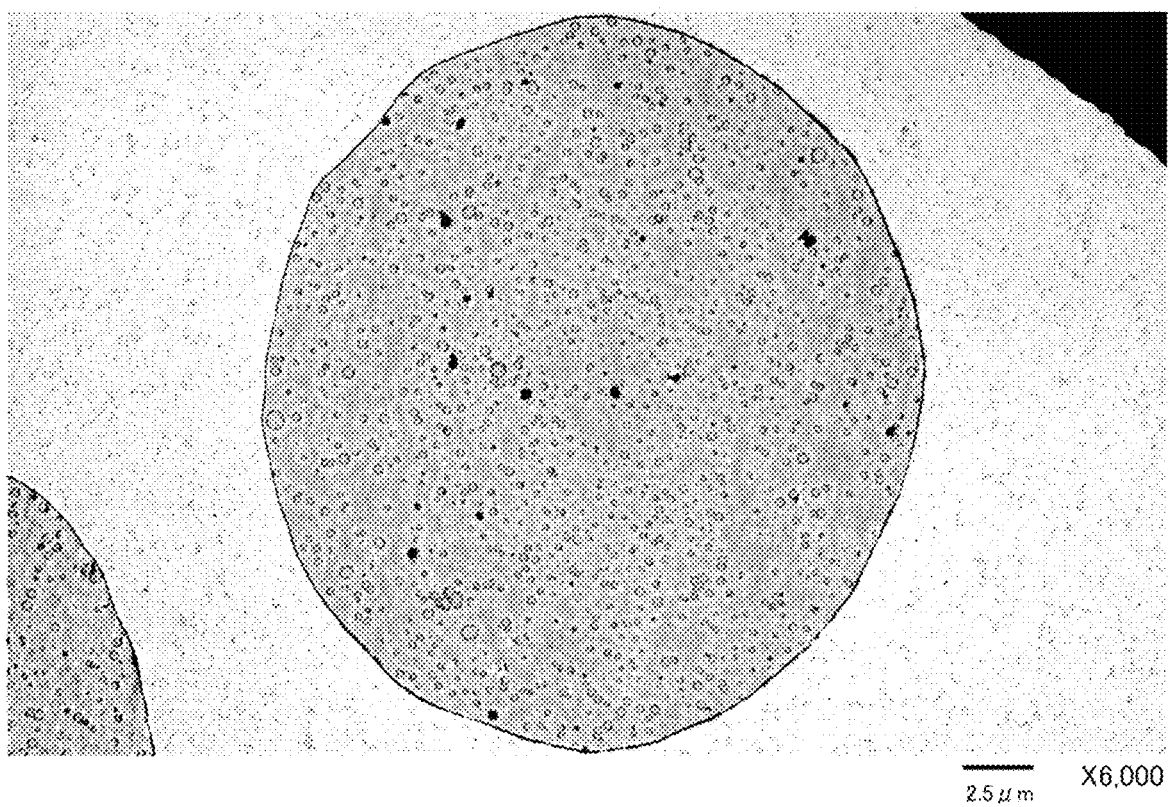
FIG. 1C is an image obtained by observing a cross section of a fiber in a spunbonded non-woven fabric in Comparative Example 1, with a transmission electron microscope.

An image obtained by observing a cross section of a fiber in the spunbonded non-woven fabric obtained in Comparative Example 1, with a transmission electron microscope, is illustrated in FIG. 1C.

TABLE 1

|  |  | Example 1 | Example 2 | Example 3 | Comparative Example 1 |
|---|---|---|---|---|---|
| Extruder (larger) | | 60 | 70 | 80 | 100 |
| Extruder (smaller) | | 40 | 30 | 20 | 0 |
| BC/MC | | BC | BC | BC | MC |
| Percentage of island phases | ≥ 0.63 μm | 0.2 | 0 | 4.6 | 1 |
| | 0.63 μm > ≥ 0.12 μm | 83.94 | 58.474 | 47.33 | 9.64 |
| | < 0.12 μm | 15.86 | 41.526 | 48.07 | 89.36 |
| Constituent [% by mass] | Propylene homopolymer having melting point of 140°C or more | 72.7 | 72.7 | 72.7 | 72.7 |
| | Propylene random copolymer (polymer (I)) | 20 | 20 | 20 | 20 |
| | Polyethylene | 7 | 7 | 7 | 7 |
| | Erucic acid amide | 0.3 | 0.3 | 0.3 | 0.3 |
| Embossment temperature [°C] | | 129 | 129 | 129 | 129 |
| Basis weight [g/m$^2$] | | 18 | 18 | 18 | 18 |
| Maximum elongation | MD direction [%] | 150 | 154 | 140 | 131 |
| | CD direction [%] | 145 | 144 | 128 | 127 |
| Maximum strength | MD direction [N/50 mm] | 28 | 29 | 28 | 30 |
| | CD direction [N/50 mm] | 17 | 17 | 16 | 18 |
| Heat-sealing property | | Present | Present | Present | Present |
| Embossment residual rate | | 58% | 57% | 58% | 57% |
| Flexibility (sensory evaluation) | | A | A | A | A |

The results in Table 1 reveal that the spunbonded non-woven fabrics of the present embodiment obtained in Examples are superior in extensibility to that in Comparative Example.

As set forth in Table 1, each of the spunbonded non-woven fabrics in Examples has not only the excellent extensibility but also a favorable heat-sealing property and a favorable embossment residual rate, and is therefore found to be excellent in stretching processing suitability. Each of the spunbonded non-woven fabrics in Examples was excellent in flexibility.

These evaluation results reveal that the spunbonded non-woven fabric of the present embodiment is preferable for applications of sanitary materials requiring extensibility, flexibility, and processing suitability.

The entire contents of the disclosures by Japanese Patent Application No. 2019-014680 filed on Jan. 30, 2019 are incorporated herein by reference. All documents, patent applications, and technical standards described in this specification are herein incorporated by reference to the same extent as if each individual document, patent application, or technical standard was specifically and individually indicated to be incorporated by reference.

The invention claimed is:

1. A spunbonded non-woven fabric, comprising a fiber comprising: a propylene homopolymer having a melting point of 140° C. or more; a polyethylene having a density of from 0.941 g/cm3 to 0.970 g/cm3; and at least one polymer selected from the group consisting of a polymer specified in the following (I) and a polymer specified in the following (II), wherein the fiber comprises a sea-island structure, and a percentage of an island phase having a diameter of from 0.12 μm to less than 0.63 μm with respect to an entire island phase in a cross section orthogonal to an axis direction of the fiber on a number basis is 30% or more:

(I) a random copolymer of propylene and at least one selected from ethylene or an α-olefin having a carbon number of from 4 to 20, and (II) a propylene homopolymer with a melting point of less than 120° C., satisfying the following (a) to (f):

(a) [mmmm]=from 20% by mol to 60% by mol,
(b) [rrrr]/(1−[mmmm])≤0.1,
(c) [rmrm]>2.5% by mol,
(d) [mm]×[rr]/[mr]$^2$≤2.0,
(e) weight-average molecular weight (Mw)=from 10,000 to 200,000, and
(f) molecular weight distribution (Mw/Mn)<4, wherein, in (a) to (d), [mmmm] represents a meso-pentad fraction, [rrrr] represents a racemic pentad fraction, [rmrm] represents a racemic meso-racemic meso-pentad fraction, each of [mm], [rr], and [mr] represents a triad fraction, and Mn represents a number-average molecular weight.

2. The spunbonded non-woven fabric according to claim 1, wherein a percentage of an island phase having a diameter of 0.63 μm or more on a number basis is 10% or less.

3. The spunbonded non-woven fabric according to claim 1, wherein a percentage of an island phase having a diameter of less than 0.12 μm on a number basis is 70% or less.

4. The spunbonded non-woven fabric according to claim 1, wherein a content of the polyethylene is from 1.0% by mass to 15.0% by mass with respect to a total amount of the fiber.

5. The spunbonded non-woven fabric according to claim 1, wherein a content of at least one polymer selected from the group consisting of the polymer specified in (I) and the polymer specified in (II) is from 5.0% by mass to 30.0% by mass with respect to a total amount of the fiber.

6. The spunbonded non-woven fabric according to claim 1, wherein a content of the propylene homopolymer having a melting point of 140° C. or more is from 55.0% by mass to 90.0% by mass with respect to a total amount of the fiber.

7. The spunbonded non-woven fabric according to claim 1, wherein the fiber comprises a fatty acid amide having a carbon number of from 15 to 22, and a content of the fatty acid amide having a carbon number of from 15 to 22 is from 0.1% by mass to 5.0% by mass with respect to a total amount of the fiber.

8. The spunbonded non-woven fabric according to claim 1, wherein the polymer specified in (I) is a random copolymer comprising at least a constitutional unit derived from propylene and a constitutional unit derived from ethylene.

9. A sanitary material, comprising the spunbonded non-woven fabric according to claim 1.

10. A method of manufacturing a spunbonded non-woven fabric, the method comprising extruding a composition comprising: a propylene homopolymer having a melting point of 140° C. or more; a polyethylene having a density of from 0.941 g/cm$^3$ to 0.970 g/cm$^3$; and at least one polymer selected from a group consisting of a polymer specified in the following (I) and a polymer specified in the following (II) such that an amount of the composition extruded from an extruding machine A and an extruding machine B is 85:15 to 55:45 (extruding machine A: extruding machine B) on a mass basis:
  (I) a random copolymer of propylene and at least one selected from ethylene or an α-olefin having a carbon number of from 4 to 20, and
  (II) a propylene homopolymer with a melting point of less than 120° C., satisfying the following (a) to (f),
  (a) [mmmm]=from 20% by mol to 60% by mol,
  (b) [rrrr]/(1−[mmmm])≤0.1,
  (c) [rmrm]>2.5% by mol,
  (d) [mm]×[rr]/[mr]$^2$≤2.0,
  (e) weight-average molecular weight (Mw)=from 10,000 to 200,000, and
  (f) molecular weight distribution (Mw/Mn)<4,
  wherein in (a) to (d), [mmmm] represents a meso-pentad fraction, [rrrr] represents a racemic pentad fraction, [rmrm] represents a racemic meso-racemic meso-pentad fraction, each of [mm], [rr], and [mr] represents a triad fraction, and Mn represents a number-average molecular weight.

11. The method of manufacturing a spunbonded non-woven fabric according to claim 10, wherein a bore A of the extruding machine A is larger than a bore B of the extruding machine B.

* * * * *